United States Patent
Fensholdt

(12) 
(10) Patent No.: US 6,531,591 B1
(45) Date of Patent: Mar. 11, 2003

(54) SYNTHESIS OF STABLE QUINONE AND PHOTOREACTIVE KETONE PHOSPHORAMIDITE REAGENTS FOR SOLID PHASE SYNTHESIS OF PHOTOREACTIVE-OLIGOMER CONJUGATES

(75) Inventor: Jef Fensholdt, Søborg (DK)

(73) Assignee: Exiqon A/S, Vedbaek (DK)

( * ) Notice: Subject to any disclaimer, the term of this patent is extended or adjusted under 35 U.S.C. 154(b) by 215 days.

(21) Appl. No.: 09/611,833

(22) Filed: Jul. 7, 2000

Related U.S. Application Data
(60) Provisional application No. 60/143,948, filed on Jul. 15, 1999.

(30) Foreign Application Priority Data
Jul. 7, 1999 (DK) ......................................... 1999 00987

(51) Int. Cl.$^7$ ............................................. C07H 21/00
(52) U.S. Cl. ...................... 536/25.34; 435/133; 558/70
(58) Field of Search ...................... 536/25.34; 435/133; 558/70

(56) References Cited

U.S. PATENT DOCUMENTS

| | | | |
|---|---|---|---|
| 3,891,327 A | 6/1975 | Welch et al. ................. | 356/244 |
| 4,016,306 A | 4/1977 | Miyagawa et al. ............ | 427/54 |
| RE31,712 E | 10/1984 | Giese ........................... | 428/407 |
| 4,722,906 A | 2/1988 | Guire ........................... | 436/501 |
| 4,737,544 A | 4/1988 | McCain et al. .............. | 525/54.1 |
| 4,822,682 A | 4/1989 | Dorsch et al. ................ | 428/411.1 |
| RE32,991 E | 7/1989 | Szycher et al. ................ | 528/75 |
| 4,892,402 A | 1/1990 | Sawamoto et al. ...... | 351/160 H |
| 4,973,493 A | 11/1990 | Guire ............................. | 427/2 |
| 5,002,582 A | 3/1991 | Guire et al. ................... | 623/66 |
| 5,214,136 A | 5/1993 | Lin et al. ....................... | 514/44 |
| 5,292,873 A | 3/1994 | Rokita et al. ................ | 536/24.3 |
| 5,304,404 A | 4/1994 | Morra et al. .................. | 427/512 |
| 5,378,502 A | 1/1995 | Willard et al. ............... | 427/305 |
| 5,391,438 A | 2/1995 | Pasternak .................... | 428/523 |
| 5,409,731 A | 4/1995 | Nakagawa et al. ......... | 427/2.12 |
| 5,427,779 A | 6/1995 | Elsner et al. .............. | 424/78.17 |
| 5,466,492 A | 11/1995 | Keissling et al. ........... | 427/522 |
| 5,482,867 A | 1/1996 | Barrett et al. ................ | 436/518 |
| 5,545,568 A | 8/1996 | Ellman ........................ | 436/518 |
| 5,650,399 A | 7/1997 | Rokita et al. .................. | 514/44 |

FOREIGN PATENT DOCUMENTS

| | | | | |
|---|---|---|---|---|
| EP | 0 155 252 | 9/1985 | ......... | G01N/33/545 |
| EP | 0 319 953 | 6/1989 | ........... | C09D/11/06 |
| EP | 0 319 957 | 6/1989 | .............. | C08J/7/12 |
| EP | 0 359 225 | 3/1990 | .............. | C07F/9/24 |
| JP | 63271410 | 3/1999 | | |
| WO | WO 87/00343 | 1/1987 | ............ | H01B/1/12 |
| WO | WO 89/05616 | 6/1989 | .............. | A61F/2/54 |
| WO | WO 90/12802 | 11/1990 | ........... | C07H/15/12 |
| WO | WO 91/02768 | 3/1991 | .............. | C08J/7/12 |
| WO | WO 96/31557 | 10/1996 | .............. | C08J/7/18 |
| WO | WO 99/43688 | 9/1999 | ............ | C07H/1/08 |

OTHER PUBLICATIONS

Aleixo, et al. "Enzyme immunoassay: binding of Salmonella antigens to activated microtiter plates" J. of Immunoassay 6 (4), 1985, p. 391–407.

Furniss, et al. "Vogels Textbook of Practical Organic Chemistry" Fifth Edition, Longmann Scientific & Technical, UK, 1989, p. 109.

Jakobsen, M.H. "Photochemical grafting of funtional groups and biomolecules onto polymer surfaces" Center for Medical Biotechnology, University of Copenhagen (Apr. 27, 1995).

Jakobsen, et al. "Immobilization of histide tagged peptides on nickel chelate derivatized microtitre plates" Presented at the 4th International Symposium, Edinburgh, 1995.

Jensen, et al. "Photochemical coupling of peptides to polystyrene microwell plates" Innovation and Perspectives in Solid Phases Synthesis & Combinatorial Libraries, 1996, p. 419–422.

Jauho, et al. "New generic method for the generation of a diagnostic surface based on bacterial polysaccharides" Poster presented at the 25th Silver Jubilee Meeting of teh Federation of European Biochemical Societies (FEBS) in Copenhagen in Jul. 1998.

Orum, et al. "Detection of the factor V Leiden mutation by direct allele–specific hybridistion of PCR amplicons to photoimmobilised Locked Nucleic Acids (LNA)" Clinical Chemistry, 45, No. 11, 1999, p. 1898–1905.

*Primary Examiner*—James O. Wilson
*Assistant Examiner*—Howard V. Owens
(74) *Attorney, Agent, or Firm*—Peter F. Corless; Dianne M. Rees; Edwards & Angell, LLP

(57) ABSTRACT

Quinone phosphoramidite reagents as well as photoreactive ketone phosphoramidite reagents, such as anthraquinone phosphoramidite reagents and benzophenone phosphoramidite reagents were synthesized and used for the solid phase synthesis of photoreactive-oligonucleotide conjugates. These phosphoramidite reagents are stable, suitable for large-scale synthesis and designed for automated solid phase synthesis of oligomers terminating in a photoreactive moiety.

22 Claims, 8 Drawing Sheets a) 3-amino-1-propanol, BOP, Et₃N, DMF. b) *N,N*-diisopropylphosphoramido-chloridite, CH₂Cl₂, DIPEA. c) *N,N,N',N'*-tetraisopropylphosphorodiamidite, tetrazole, CH₂Cl₂, CH₃CN.

a) 3-amino-1-propanol, BOP, Et₃N, DMF. b) 2-cyanoethyl *N,N,N',N'*-tetraisopropyl-phosphorodiamidite, tetrazole, CH₂Cl₂, CH₃CN

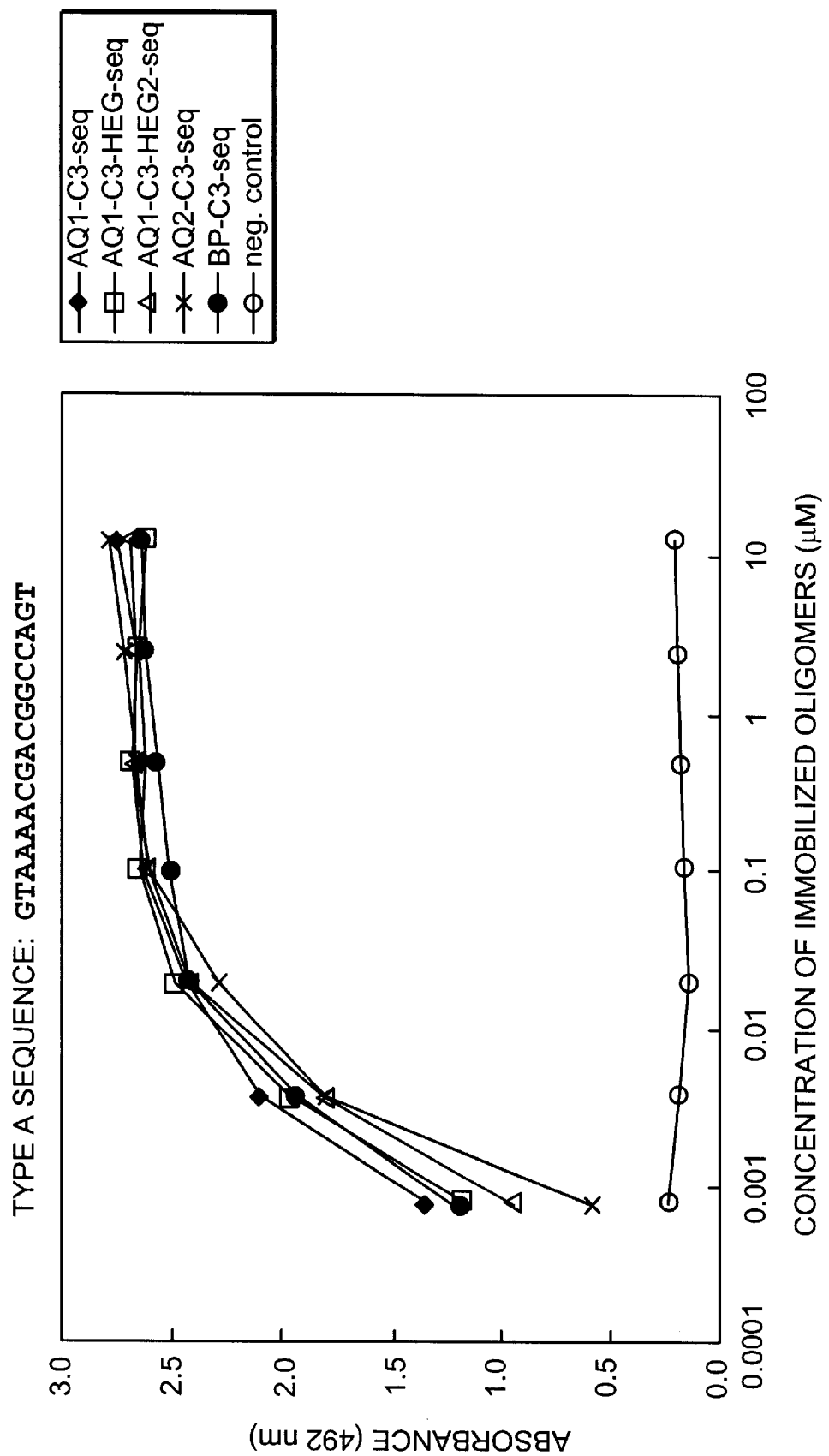

SYNTHESIS OF STABLE QUINONE AND PHOTOREACTIVE KETONE PHOSPHORAMIDITE REAGENTS FOR SOLID PHASE SYNTHESIS OF PHOTOREACTIVE-OLIGOMER CONJUGATES

This application claims the benefit of Provisional Application No. 60/143,948, filed Jul. 15, 1999.

FIELD OF THE INVENTION

The present invention relates to the field of stable quinone- and photoreactive ketone phosphoramidite reagents designed for automated solid phase synthesis of oligomers terminating in a photoreactive moiety.

BACKGROUND OF THE INVENTION

Attachment of a reporter group or another conjugation to oligonucleotides (ONs) has been the subject of considerable research as the resulting functionalised ONs display great potential as diagnostic or therapeutic agents (S. L. Beaucage, *Comprehensive Natural Products Chemistry* Vol. 7. Ed. E. T. Kool, Editors-in-Chief D. Barton and K. Nakanishi, Pergamon, 1999, 153–250). For example, ONs linked to anthraquinone (anthraquinone-ONs) and derivatives thereof have been prepared with the purpose of increasing the affinity towards complementary ONs via intercalation as well as for studies of site specific modification, cleavage, and crosslinking of duplex structures (K. Mori et al., *FEBS lett.* 1989, 249, 213–218; S. M. Gasper and G. B. Schuster, *J. Am. Chem. Soc.* 1997, 119, 12762–12771; L. G. Puskás et al., *Nucleosides Nucleotides*, 1995, 14, 967; H. Kang and S. E. Rokita; *Nucleic acids Res.*, 1996, 24, 3896–3902). Another interesting application of anthraquinone-oligomers is the covalent immobilization of oligomers onto polymeric surfaces. Immobilisation of oligomers on various surfaces (Jacobsen, M. H. and Koch, T. WO 96/31557, 1996), such as plastic microtiter plates, microchips and micro particles has been achieved by various means and form the basis for a rapidly expanding technology within the field of diagnostic assays and disease screening assays (F. N. Rehman et al., *Nucleic acids Res.*, 1999, 27, 649–655; P. W. Stevens et al., *Nucleic acids Res.*, 1999, 27, 1719–1727; G. Ramsay, *Nature Biotechnology*, 1998, 16, 40–44).

Two general methods for covalent attachment of anthraquinone to oligomers by chemical means have previously been developed. The first method comprises coupling of an activated anthraquinone derivative with a pre-synthesized oligomer containing a reactive group such as a free primary amine function. This approach is illustrated by Kang and Rokita (*Nucleic Acids Res.*, 1996, 24, 3896–3902) who synthesized 5'-end anthraquinone-oligodeoxynucleotides (ODNs) for the studies of site-specific and photo-induced alkylation of DNA. A dimethyl-anthraquinone-ODN conjugate was synthesized by coupling of the N-hydroxysuccinimide ester of 2-(3-propionic acid)-1,4-dimethylanthraquinone with 5'-amino hexamethylene linked ODN, obtained by standard automated solid phase synthesis. Anthraquinone-ONs have also been prepared by reaction of ONs containing "amino -linker" modified nucleobases or carbohydrate moieties with activated anthraquinone derivatives (Telser et al. *J. Am. Chem. Soc.* 1989, 111, 7226–7232; Akira et al. *Bioconjugate Chem.* 1993, 4, 499–508).

The other method comprises converting the anthraquinone into a synthon that can be used for automated solid phase synthesis, e.g. coupling of the anthraquinone to a phosphoramidite reagent. Depending on the availability of the building-block it can be argued that this direct incorporation is the most efficient approach, as the total synthesis of the anthraquinone-oligomers can be performed on an automated synthesizer.

Attachment of anthraquinone derivatives to ONs via direct incorporation has been approached by linking the anthraquinone group to the 2'-O position of a 5'-O-DMT (4,4'-dimethoxytrityl), 3'-O-phosphoramidite nucleoside reagents. K. Yamana et al. (*Bioconjugate Chem.* 1996, 7, 715–720) reported the synthesis of 5'-O-dimethoxytrityl 2'-O-(2-anthraquinonylmethyl)uridine 3'-O-cyanoethyl)-N,N-diisopropylphosphoramidite which was used for automated solid phase synthesis of anthraquinone-ONs.

De Mesmaeker et al. (*Bioorganic, Medicinal Chem.* 1997, 7, 1869–1874) described the synthesis of nucleoside dimers containing a 3'-5' amide bond, wherein the nitrogen atom is attached to an anthraquinone molecule through a polymethylene linker. DMT-protection of the 5'-O position and phosphitylation of the 3'-O-position of the dimer afforded a reagent suitable for automated synthesis of anthraquinone-ONs.

A non-basic pseudonucleoside bearing an anthraquinone moiety has been prepared by K.-Y., Lin and M. Matteucci (*Nucleic Acids Res.* 1991, 19, 3111–3114, and U.S. Pat. No. 5,214,136). Starting from 2-chloro anthraquinone and diethanol amine an anthraquinone diol derivative was obtained which was converted into a DMT H-phosphonate reagent which was, subsequently, incorporated multiple times into an ODNs.

The above mentioned reagents allow incorporation of an anthraquinone functionality at different positions in an oligomer.

A few examples of phosphoramidite reagents not derived from nudeosides, developed exclusively for incorporation of anthraquinone at the 5'-terminus of an oligomer using automated solid phase synthesis have been reported.

K. Mori et al. (*FEBS Lett.* 1989, 249, 213–218) describe the synthesis of anti-HIV active 5'-linked anthraquinone-ODNs wherein an anthraquinone derivative is linked to an oligodeoxynucleotide (ODN) via either an ethylpiperazinyl or a hexamethylene linker. The 5'-linked anthraquinone-ODNs were obtained by coupling of a freshly prepared anthraquinone-ethylpiperazinyl phosphoramidite (obtained in 65% yield) or anthraquinone hexamethylene-linked phosphoramidite to the 5'-end of an ODN sequence using standard automated solid phase synthesis.

The anthraquinone-ethylpiperazinyl phosphoramidite reagent has also been described in WO 90/12802. The anthraquinone phosphoramidite was synthesised using the same procedure as described by K. Mori et al.: 1-chloroanthraquinone was reacted with 1-(2-hydroxyethyl) piperazine affording 1-(1-(2-hydroxyethyl)piperazinyl) anthraquinone which was phosphitylated by N,N-diisopropylphosphoramidochloride in the presence N,N-diisopropylethylamine to afford anthraquinone-ethylpiperazinyl phosphoramidite. The anthraquinone phosphoramidite was used without further purification in the automated solid phase synthesis of 5'-linked anthraquinone-ODNs used for attenuation or destruction of mammalian genetic expression or viral activity.

S. M. Gasper and G. B. Schuster (*J. Am. Chem. Soc.* 1997, 119, 12762–12771) described the synthesis of 5'-linked anthraquinone-ODNs with the purpose of establishing the fact that oxidative damage can migrate in double-stranded DNA. For this purpose, two anthraquinone phosphoramidites were synthesised: N-ethyl- and N-pentyl-2-anthraquinonecarboxamide phosphoramidite. The two phosphoramidites were synthesised from anthraquinone-2-carbonyl chloride, which was reacted with 2-amino-1-ethanol or 5-amino-pentanol to afford N-(2-hydroxyethyl)- and N-(5-hydroxypentyl)-2-anthraquinone-carboxamide, respectively. Reaction of these carboxamides with N,N-diisopropylmethyl-phosphonamides chloride afforded the corresponding phosphoramidites as thick dark red oils after column chromatography. Coupling of these anthraquinone phosphoramidites to the 5'-OH terminus of ODNs as the final step in a solid phase synthesis gave anthraquinone-ODN conjugates.

Large scale synthesis of anthraquinone-oligomer conjugates using automated solid phase chemistry requires readily available and relatively stable anthraquinone synthons. Initial attempts to synthesize stable anthraquinone phosphoramidite reagents revealed that the above-mentioned types of reagents appear to be unstable.

The synthesis of an anthraquinone phosphoramidite derivative of N-(6-hydroxyhexyl)-2-anthraquinone carboxamide using N,N,N',N'-tetraisopropylphosphorodiamidite and tetrazole is described in Example 1. Attempted isolation of this cyanoethyl phosphoramidite led to decomposition. Use of the crude product, after filtration of the reaction mixture, directly onto the DNA synthesizer within one day also led to decomposition. Following, attempts to prepare a cyanoethyl phosphoramidite analog of the N-(2-hydroxyethyl) anthraquinonecarboxamide by reaction of N-(2-hydroxyethyl)anthraquinonecarboxamide with 2-cyanoethyl N,N-diisopropylphosphoramidochloridite in the presence of ethyldiisopropyl amine (see Example 2) or by the same procedure as described in Example 1 afforded, initially, a bright yellow foam after flash chromatography. Drying of this material under high vacuum over night resulted in a dark brown syrup, indicating decomposition. The fact that all of the above anthraquinone phosphoramidite reagents have to be used immediately after preparation makes them less suitable for synthesis of a large-scale synthesis of anthraquinone-oligomer conjugates.

SUMMARY OF THE INVENTION

The present invention relates to a stable phosphoramidite reagent, designed for automated solid phase synthesis of oligomers, of the general formula I

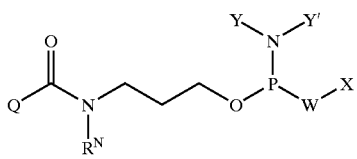
(I)

wherein Y and Y' each independently are selected from optionally substituted $C_{1-6}$-alkyl or Y and Y' together with the nitrogen to which they are bonded form a non-aromatic N-heterocyclic ring; W is selected from O and S; X is selected from optionally substituted $C_{1-6}$alkyl and optionally substituted benzyl; $R^N$ is selected from hydrogen $C_{1-4}$alkyl, optionally substituted benzyl, optionally substituted quinones, and nucleosides; and Q is selected from optionally substituted quinones, and optionally substituted photoreactive ketones, such as optionally substituted benzophenone.

The invention also relates to an oligomer comprising the following fragment:

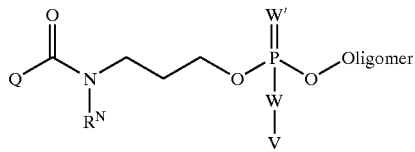

wherein Q and $R^N$ are as defined above for formula (I); W and W' are independently selected from O and S; and V is selected from optionally substituted $C_{1-6}$-alkyl, optionally substituted benzyl, hydrogen, $Li^+$, $K^+$, $Na^+$, and $NH_4^+$.

The present invention furthermore relates to a stable phosphoramidite reagent of the general formula II

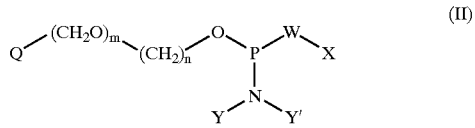
(II)

wherein Y and Y' each independently are selected from optionally substituted $C_{1-6}$-alkyl or Y and Y' together with the nitrogen to which they are bonded form a non-aromatic N-heterocyclic ring; X is selected from optionally substituted $C_{1-6}$-alkyl and optionally substituted benzyl; W is selected from O and S; Q is selected from optionally substituted quinones and optionally substituted photoreactive ketones; n is an integer from 1 to 10; and m is 0 or 1.

The invention also relates to an oligomer comprising the following fragment:

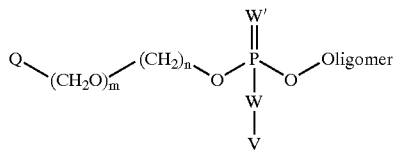

wherein Q, n and m are as defined above for formula (II); W and W' are independently selected from O and S; and V is selected from optionally substituted $C_{1-6}$-alkyl, optionally substituted benzyl, hydrogen, $Li^+$, $K^+$, $Na^+$, and $NH_4^+$.

DETAILED DESCRIPTION OF THE INVENTION

The applicant has successfully approached covalent coupling of synthetic oligomers onto carbon-containing polymers in two different ways. In the first approach, a photoprobe, consisting of an anthraquinone or benzophenone molecule linked to an electrophilic reactive group via an ethylene glycol linker, was coupled to a polymer surface by short time exposure to UV light. Subsequently, reaction between the electrophilic groups attached to the polymer and nucleophilic aminoalkyl ONs lead to immobilization of the oligomers.

The second approach involved automated solid phase synthesis of anthraquinone-oligomers or benzophenone-oligomers. Irradiation of an aqueous solution containing either the anthraquinone-oligomers or benzophenone-oligomers with soft UV light resulted in attachment of the anthraquinone-oligomers and benzophenone-oligomers to the polymer surface through a covalent bond between the anthraquinone moiety or benzophenone moiety and the surface to which the solution has been applied.

The present invention describes the synthesis of surprisingly stable quinone- and photoreactive ketone phosphoramidite reagents which do not suffer from the drawbacks described above. These new reagents are easily synthesised from commercially available starting materials. Contrary to previous described 5'-end anthraquinone labelling phosphoramidites, the phosphoramidite reagents according to the present invention are isolated as stable solid materials, which can be stored for several months at −20° C. without loss of reactivity and incorporated in an oligomer, using standard automated solid phase synthesis. Similarly, benzophenone phosphoramidites according to the present invention are isolated as stable oils, which can be stored for several months at −20° C. without loss of reactivity and incorporated in an oligomer, using standard automated solid phase synthesis.

As mentioned above, the present invention i.a. relates to a stable phosphoramidite reagent of the general formula I

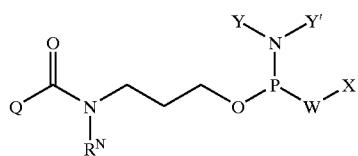
(I)

wherein Y and Y' each independently may designate an optionally substituted $C_{1-6}$-alkyl or Y and Y' together with the nitrogen to which they are bonded form a non-aromatic N-heterocyclic ring.

Among the possible Y and Y', the situation where Y and Y' each designate ethyl or isopropyl, or together designate pyrrolidino, piperidino or morpholino seem especially interesting, and the situation where Y and Y' both are isopropyl appears to be particularly interesting.

The substituent X is selected from the group consisting of optionally substituted $C_{1-6}$-alkyl and benzyl. Examples of optionally substituted $C_{1-6}$-alkyl are methyl, 2-cyanoethyl, 2-(4-nitrophenyl)ethyl, 2-(2-pyridyl)ethyl, 2-(4-pyridyl) ethyl, and 2-($C_{1-6}$-alkylsulfonyl)ethyl among which 2-cyanoethyl presently is the most preferred.

W is selected from O and S where O is most preferred.

$R^N$ is selected from hydrogen and $C_{1-4}$-alkyl, such as methyl, ethyl, and isopropyl, optionally substituted benzyl, optionally substituted quinones attached via suitable linkers, e.g. methylene and polymethylene, and nucleosides attached via 5'-C through a methylene or polymethylene linker; preferably $R^N$ designates hydrogen.

Q represents a group selected from optionally substituted quinones and optionally substituted photoreactive ketones.

By the term "quinone" is understood a dihydroaromatic system wherein the —CH$_2$— groups are replaced by —C(=O)—. In the present context "quinone" covers quinones derived from di- or tetrahydroaromatic systems comprised by 1 to 5 fused carbon cyclic rings. illustrative examples of such quinones are derived from 1,4benzoquinone, 1,2-benzoquinone, naphtoquinone, anthraquinone, phenanthrenequinone, alizarin, rubiadin, lucidin, damnacanthal, munjistin, chrysophanol, frangulaemodin, aloe-emodin, morindone, and copareolatin. As mentioned above, quinones may be optionally substituted, however, it is presently believed that unsubstituted quinones, in particular unsubstituted anthraquinone and phenanthrenequinone, are especially preferred.

Examples of particular interesting photoreactive ketones are acetophenone, benzophenone, anthrone and anthrone-like heterocycles, i.e. anthrone wherein the group in 10-position is replaced by O, S, or NH. The photoreactive ketones can be optionally asubstituted as described below. Particular interesting photoreactive ketones are benzophenone and acetophenone of which unsubstituted benzophenone is presently most preferred.

In a preferred embodiment of the present invention, the phosphoramidite has the following structure:

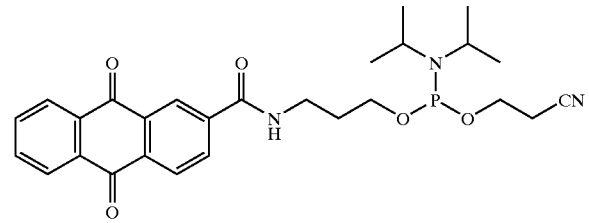

In a preferred embodiment of the present invention, the phosphoramidite has the following structure:

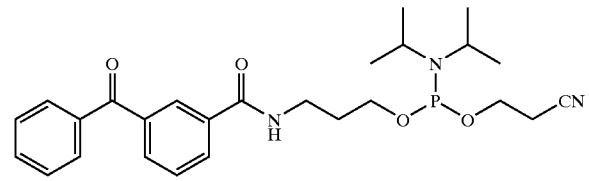

When coupled to oligomers, e.g. ONs or ODNs, the reagents of the present invention lead to a novel class of oligomers. Thus, the invention furthermore relates to an oligomer comprising the following fragment:

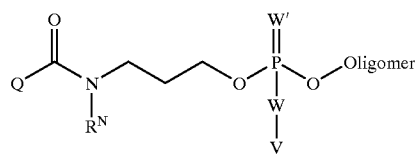

wherein Q and $R^N$ are as defined above for formula (I), W and W' are independently selected from O and S, V is selected from optionally substituted $C_{1-6}$-alkyl, optionally substituted benzyl, hydrogen, Li$^+$, K$^+$, Na$^+$, and NH$_4^+$ and "oligomer" has the meaning defined below. In a preferred embodiment, Q represents anthraquinone, $R^N$ represent hydrogen, W and W' both represent O, and V is hydrogen.

The invention also relates to a phosphoramidite reagent of the formula II

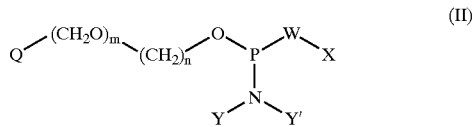
(II)

wherein Y and Y' each independently may designate an optionally substituted $C_{1-6}$alkyl or Y and Y' together with the nitrogen to which they are bonded form a non-aromatic N-heterocyclic ring.

Among the possible Y and Y', the situation where Y and Y' each designate ethyl or isopropyl, or together designate pyrrolidino, piperidino or morpholino seem especially interesting, and the situation where Y and Y' both are isopropyl appears to be particularly interesting.

The substituent X is selected from the group consisting of optionally substituted $C_{1-6}$-alkyl and benzyl. Examples of optionally substituted $C_{1-6}$-alkyl are methyl, 2-cyanoethyl, 2-(4-nitrophenyl)ethyl, 2-(2-pyridyl)ethyl, 2-(4-pyridyl)ethyl, and 2-($C_{1-6}$-alkylsulfonyl)ethyl among which 2-cyanoethyl presently is the most preferred.

W is selected from O and S where O is most preferred.

Q represent a group selected from optionally substituted quinones and optionally substituted photoreactive ketones. Illustrative examples of such quinones are derived from phenanthrenequinone, 1,4-benzoquinone, 1,2-benzoquinone, naphtoquinone, anthraquinone, alizarin, rubiadin, lucidin, damnacanthal, munjistin, chrysophanol, frangula-emodin, aloe-emodin, morindone, and copareolatin. As mentioned above, quinones may be optionally substituted, however, it is presently believed that unsubstituted quinones, in particular unsubstituted anthraquinone and phenanthrenequinone, are especially preferred.

Examples of particular interesting optionally substituted photoreactive ketones are benzophenone, amino-, hydroxyl-, halogen-, acyl-, nitro-, and cyanobenzophenone, of which unsubstituted benzophenone is presently most preferred.

n is an integer from 1 to 10. It is presently believed that variants where n is ranging from 1 to 4, such as 1, 2, 3 or 4, are particularly relevant.

m is 0 or 1.

In a preferred embodiment, Y and Y' both are isopropyl and X designates 2-cyanoethyl Coupling of phosphoramidite reagents of the general formula II to the termini of an oligomer affords oligomers containing the following fragment. Thus, the invention also relates to an oligomer comprising this fragment:

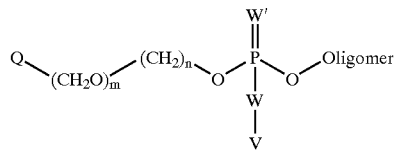

wherein Q, n and m are as defined above for formula (II), W and W' are independently selected from O and S, and V is selected from optionally substituted $C_{1-6}$-alkyl, optionally substituted benzyl, hydrogen, $Li^+$, $K^+$, $Na^+$, and $NH_4^+$ and "oligomer" has the meaning defined below. In a preferred embodiment, Q represents anthraquinone or phenanthrenequinone, W and W' both represent O, V is hydrogen, n is 1, and m is 0.

It should also be understood that the phosphoramidite reagents of the general formulas I and II can be coupled to the 3'-OH termini of an oligomer synthesized from 5'→3'.

Preparation of Phosphoramidite Reagents

In a preferred embodiment, anthraquinone phosphoramidites were synthesised by the following procedures:

Synthesis of the anthraquinone phosphoramidite 3 is illustrated in FIG. 1 and was performed in two steps starting from commercially available anthraquinone-2-carboxylic add (1). Coupling of compound 1 with 3amino-1-propanol in the presence of benzotriazol-1-yloxytris(dimethylamino)-phosphonium hexaflourophosphate (BOP) yielded the amide 2. Subsequently, phosphitylation of 2 using 2-cyanoethyl-N,N-diisopropylphosphoramido-chloridite afforded the anthraquinone phosphoramidite 3 as a red oil after aqueous workup. Redissolution of the crude product 3 in a minimum amount of anhydrous methylenechloride and subsequent precipitation in vigorously stirred petroleum ether at 0° C. afforded 3 as a bright yellow powder. The product 3 was dried overnight at high vacuum and stored under nitrogen at −20° C.

Synthesis of the anthraquinone phosphoramidite 5 is illustrated in FIG. 1 and was performed in one step starting from commercial available 2-(hydroxymethyl) anthraquinone (4). Phosphitylation of 2-(hydroxymethyl) anthraquinone (4) using the same procedure as described for the preparation of 3 afforded the corresponding phosphoramidite 5 as a yellow oil, which was coevaporated with anhydrous acetonitrile to afford 5 as a yellow solid material.

Alternatively, reaction of 2-(hydroxymethyl) anthraquinone (4) with 2-cyanoethyl-N,N,N',N'-tetraisopropylphosphorodiamidite and tetrazole afforded the phosphoramidite 5 as a bright yellow solid material after filtration and aqueous workup.

Phosphoramidite 3 has been used in automated solid phase synthesis for a large number of anthraquinone-ODN conjugates. The phosphoramidite 3 was coupled directly to the 5'-OH termini of an ODN or via a 5'-hexaethyloxyglycol spacer (Spacer™) to an ODN as the final step in an automated solid phase synthesis on a Gene Assembler Special® synthesiser using a 0.1 M solution and a 5 min. coupling time. The coupling efficiency was estimated to be >98% as attempted coupling of another thymidine nucleoside (T) residue to a test sequence 5'-anthraquinone-T-3' failed completely (no 4,4'-dimethoxytrityl-release was monitored). The two general types of anthraquinone oligonucleotide synthesised are illustrated in FIG. 2.

In a preferred embodiment, optionally substituted photoreactive ketone phosphoramidites, such as benzophenone phosphoramidites, were synthesised by the following procedures:

Synthesis of the anthraquinone phosphoramidite 8 was performed in two steps starting from commercially available benzoylbenzoic acid (6). Coupling of compound 6 with 3-amino-1-propanol in the presence of benzotriazol-1-yloxytris(dimethylamino)-phosphonium hexaflourophosphate (BOP) yielded the amide 7. Subsequently, phosphitylation of 7 using 2-cyanoethyl-N,N-diisopropylphosphoramido-chloridite afforded the benzophenone phosphoramidite 8 as a pale yellow oil. This oil was used without further purification and stored under nitrogen at −20° C.

FIG. 3 illustrates the synthesis of a benzophenone-phosphoramidite reagent. Its application for the preparation of benzophenone-oligonucleotide conjugates was analogous to that outlined in FIG. 2 for anthraquinone oligonucleotide conjugates.

Phosphoramidite 8 has been used in automated solid phase synthesis for a large number of anthraquinone-ODN conjugates. The phosphoramidite 8 may be coupled directly to the 5'-OH termini of an ODN or via a 5'-hexaethyloxyglycol spacer (Spacer™) to an ODN as the final step in an automated solid phase synthesis on a Gene Assembler Special® synthesiser using a 0.2 M solution and a 15 min. coupling time.

DNA oligomers carrying a 5'anthraquinone or a 5'benzophenone can be covalently immobilised on a solid support by irradiation and the immobilised oligomers are efficient in the capture of a complementary DNA oligomer.

As shown in FIGS. 6 and 7, both the AQ oligomers and the BP oligomers yield a clearly concentration dependent signal. When using a non-complementary sequence, no signal could be detected. It is concluded that both anthraquinone and optionally substituted photoreactive ketone oligomers, such as AQ and BP oligomers, can be covalently attached to a solid surface by irradiation and that oligomers attached in this way are able to hybridise to their complementary target DNA oligomers.

Definitions

In the present context, the term "$C_{1-6}$alkyl" means a linear, cyclic or branched hydrocarbon group having 1 to 6 carbon atoms, such as methyl, ethyl, propyl, isopropyl, pentyl, cyclopentyl, hexyl, cyclohexyl, preferred examples of "$C_{1-6}$-alkyl" are ethyl, propyl, iso-propyl, butyl, tert-butyl, isobutyl, pentyl, cyclopentyl, hexyl, cyclohexyl, in particular ethyl. Analogously, the term "$C_{1-4}$-alkyl" means a linear, cyclic or branched hydrocarbon group having 1 to 4 carbon atoms, such as methyl, ethyl, propyl, iso-propyl, butyl, iso-butyl, and tert-butyl.

In the present context, i.e. in connection with the terms "alkyl", "quinone" and "photoreactive ketones", the term "optionally substituted" means that the group in question may be substituted one or several times, preferably 1–4 times, with group(s) selected from hydroxyl, amino, halogen, acyl, nitro and cyano, $C_{1-6}$-alkoxy, $C_{1-6}$-alkyl (only relevant for quinone and photoreactive ketones), formyl, carboxyl, $C_{1-6}$-alkoxycarbonyl, $C_{1-6}$-alkylcarbonyl, aryl, aryloxycarbonyl, arylcarbonyl, heteroaryl, mono- and di($C_{1-6}$-alkyl)amino, carbamoyl, mono- and di($C_{1-6}$-alkyl)aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkylcarbonylamino, carbamido, where $C_{1-6}$-alkyl, aryl and heteroaryl may be substituted 1–5 times, preferably 1–3 times, with hydroxyl, acyl, $C_{1-4}$-alkyl, $C_{1-4}$-alkoxy, nitro, cyano, amino or halogen.

"Halogen" includes fluoro, chloro, bromo, and iodo.

In the present context, the term "oligomer(s)" means oligonucleotides (ONs), oligodeoxynucleotides (ODNs), and derivatives thereof, such as ONs/ODNs modified in the carbohydrate moiety, e.g. Locked Nucleoside Analogues (LNAs), ONs/ODNs modified in the phosphodiester linkaged, e.g. phosphorothioates, phosphoramidates, and methylphosphonates, ONs/ODNs modified in the heterocyclic base, and "backbone" modified ONs/ODNs, e.g. Peptide Nucleic Acids (PNAs). The oligomers may be from 1–1000 units, e.g. 1–1000 nucleotides, preferably 1–200, even more preferably 5–30 units, and each oligomer may comprise different classes of units, e.g. ODN-LNA conjugate. It should also be understood that the term "oligomer" means oligomers synthesized from 3'→5, terminating in a 5'-OH, as well as oligomers synthesized from 5'→3', terminating in a 3'-OH.

The 6 scans represent one array each. Each array is an individual analysis and is performed on individual slides. Before hybridisation with a sample, an array of AQ-oligonucleotides has been arranged on the slides and immobilised via UV-irradiation. The template after which the spots on the array are arranged is illustrated below:

| Neg | ON8 | ON8 | ON7 |
| ON9 | ON7 | Neg | ON9 |
| ON9 | Neg | ON7 | ON8 |
| ON7 | ON8 | ON9 | Neg | wherein Neg represents a negative control, ON8 is a mutant catching probe, ON7 is a positive control, and ON9 is a wildtype catching probe. This pattern is repeated 4 times (2×2) on each slide.

The 6 samples analysed here are:
1. A homogeneous wildtype including a positive control.
   Only the "wildtype spots" and the "positive control spots" light up on this slide, and thus it is possible to determine the "genotype" of the analysed sample to be homogeneous wildtype.
2. A homogeneous mutant including a positive control.
   Only the "mutant spots" and the "positive control spots" light up on this slide, and thus it is possible to determine the "genotype" of the analysed sample to be homogeneous mutant.
3. A heterozygote including a positive control.
   Both the "wildtype spots", the "mutant spots" and the "positive control spots" light up on this slide, and thus it is possible to determine the "genotype" of the analysed sample to be heterogeneous wildtype.
4. A heterozygote without positive control.
   As in 3), both the "wildtype spots", the "mutant spots", and thus it is possible to determine the "genotype" of the analysed sample to be heterogeneous wildtype. The "positive control spots" does not light up as no positive control oligo was added to the sample during preparation, thus it is possible to rule out "cross talk"/unspecific hybridisation of the samples to the positive control spots.
5. Positive control alone.
   Since no sample is present during hybridisation only the positive control spots light up, thus it is possible to rule out "cross tall" between the positive control and the "wildtype" and "mutant spots".
6. Blank (negative control).
   When an array is hybridised with a buffer containing no sample or controls, no signal is obtained from any of the spots.

Figure 5A:
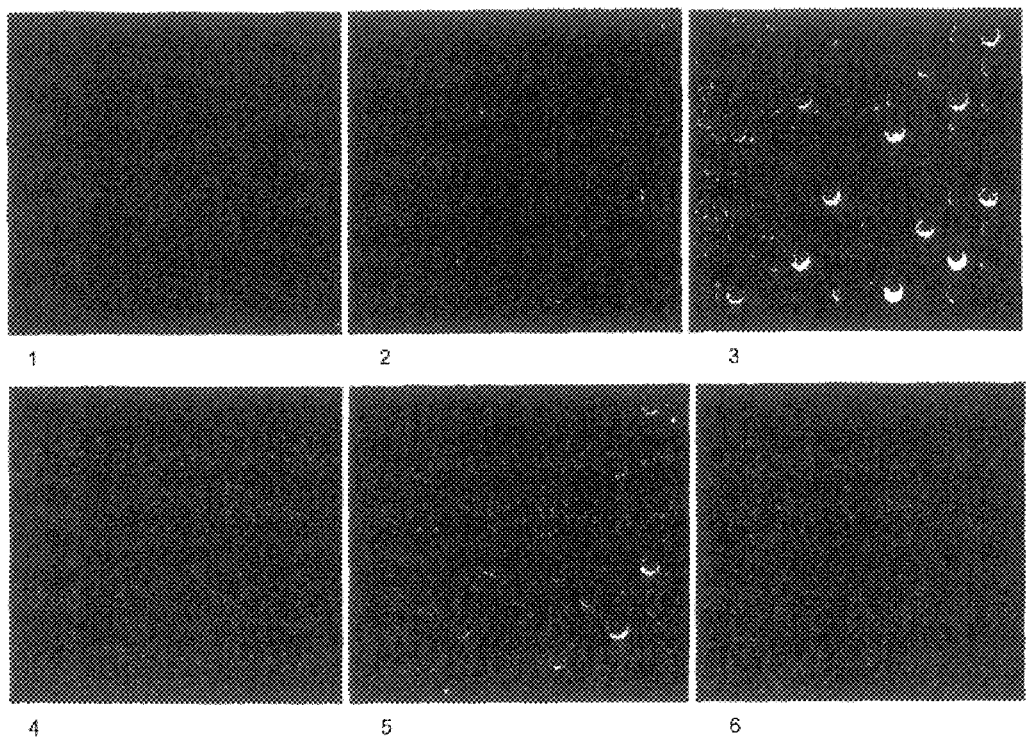
FIG. 5
Figure 5B:
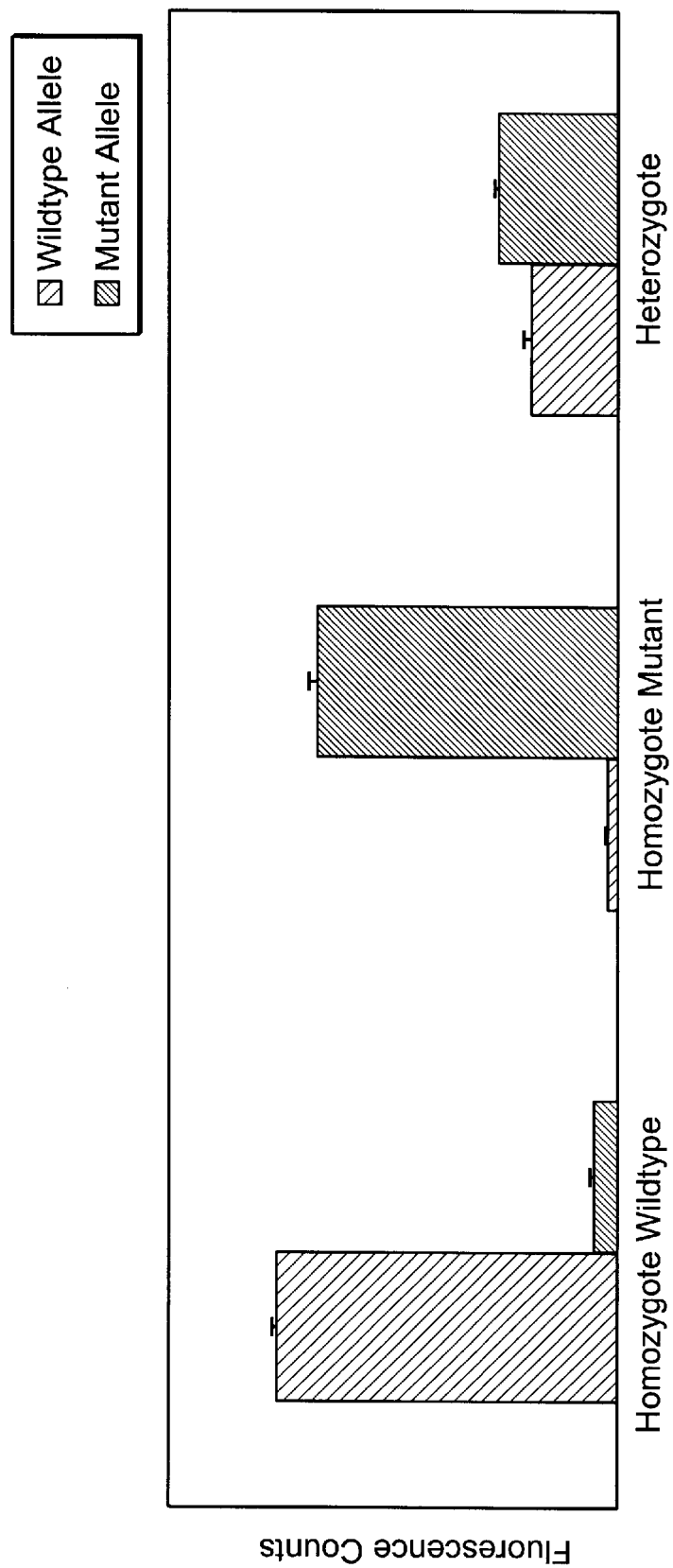

The signal strength from the mutant and the wildtype spots in slide 1, 2 and 3 were quantified with a dedicated program (Optiquant), and the results presented as a bar diagram in FIG. 5B.

FIG. 6 illustrates the immobilisation efficiency as a function of anthraquinone and benzophenone coupled oligonucleotide in 0.2 M NaCl of type A sequence.

Figure 7:
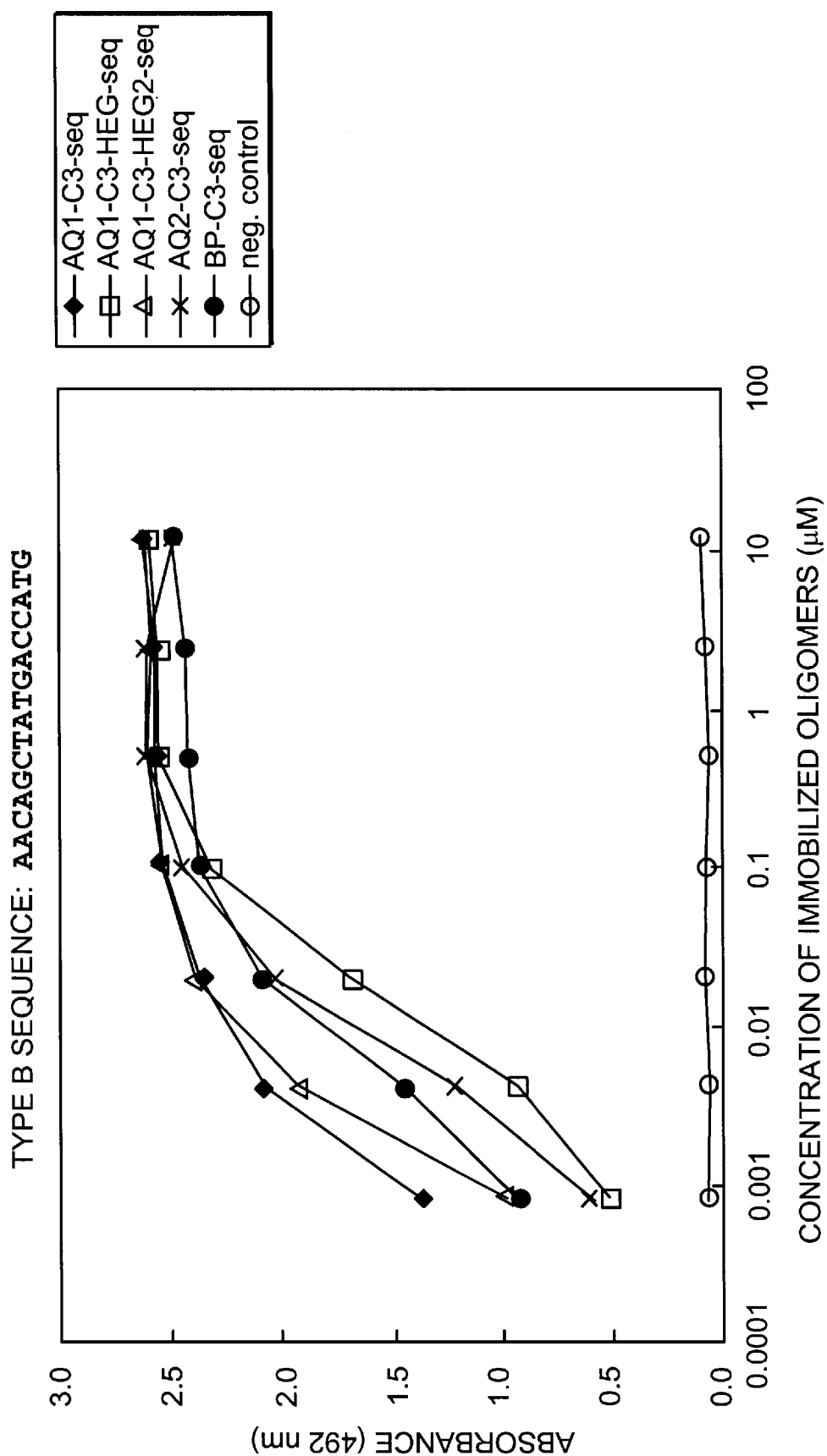

FIG. 7 illustrates the immobilisation efficiency as a function of anthraquinone and benzophenone coupled oligonucleotide in 0.2 M NaCl of type B sequence.

EXPERIENTIAL

Example 1

N-(6hydroxyhexyl)-2-anthraquinone carboxamide (193 mg, 0.55 mmol) was dried by evaporation once with dry acetonitrile and suspended in dry acetonitrile (5 ml) under nitrogen. To this suspension was added 2-cyanoethyl N,N,N',N'-tetraisopropyl-phosphorodiamidite (150 mg, 0.50 mmol) and tetrazole (1.0 ml of a 0.43 M solution in acetonitrile, 0.43 mmol). The mixture was stirred and heated to 40° C. for 1 h, stirred overnight at room temperature, and heated to 40° C. for a further period (usually 3–4 h), until $^{31}$P-NMR showed that all the phosphorus reagent had reacted (signals at 123 and 132 ppm absent, the product is at 146.4 ppm). The reaction mixture (a thick slurry) was filtered under nitrogen (Bio-Rad Poly-Prep Column used as filter) and the residue washed with dry acetonitrile to bring the filtrate to ca. 5 ml. This solution (ca. 0.1 M in phosphoramidite) was used directly on the DNA synthesizer within a day. The phosphoramidite slowly decomposes in solution at room temperature, and attempts to isolate it resulted in decomposition.

Example 2

To a suspension of N-(2-hydroxyethyl)-2-anthraquinone carboxamide (500 mg, 1.69 mmol) in dry $CH_2Cl_2$ (5 ml) under $N_2$, was added diisopropylethyl amine (1.0 ml, 5.74 mmol) followed by dropwise addition of 2-cyanoethyl N,N-diisopropylphosphoramido-chloridite (0.38 ml, 1.70 mmol). The resulting clear yellow solution was stirred at room temperature for 30 min, then poured into ethyl acetate (10 ml) containing triethylamine (1 ml). The mixture was washed with saturated aqueous $NaHCO_3$ (2×5 ml) and brine (2×5 ml), dried ($Na_2SO_4$) and evaporated under reduced pressure. The residue was subjected to column chromatography on silica gel (eluent: 45:45:10, ethyl acetate:petroleum ether:triethyl amine) and gave 640 mg of a yellow syrup, which turned into a dark red gum after drying overnight under high vacuum.

Treatment of N-(2-hydroxyethyl)-2-anthraquinone carboxamide (510 mg, 1.73 mmol) with 2-cyanoethyl N,N,N',N'-tetraisopropylphosphorodiamidite (0.55 ml, 1.73 mmol) and tetrazole (3.65 ml of a 0.45 M solution in acetonitrile, 1.64 mmol) in dry $CH_2Cl_2$ (20 ml) for 120 min. at room temperature, gave after filtration of the reaction mixture and aqueous workup and evaporation of the solvents a yellow foam, which collapsed into a dark-brown syrup after drying overnight under high vacuum.

Example 3

Preparation of N-(3-hydroxypropyl)-2-anthraquinonecarboxamide (2)

To a stirred suspension of anthraquinone-2-carboxylic acid (Aldrich, 10.00 g, 39.64 mmol) in DMF (130 ml), was added (benzotriazol-1-yloxy)tris(dimethylamino)-phosphonium hexafluorophosphate (17.54 g, 39.66 mmol) and trethylamine (11.05 ml, 79.28 mmol). The resulting mixture (initially a clear green solution) was stirred at room temperature for 10 min. before dropwise addition of 3-amino-1-propanol (3.34 ml, 43.67 mmol). The reaction mixture (clear brown solution) was stirred at room temperature in the dark for 17 hours. The solution was poured in a thin stream into water (300 ml) containing some ice. The precipitated material was isolated by filtration and recrystallised from boiling 96% ethanol (ca. 200 ml) and gave the title compound 2 as a bright yew solid (6.93 g, 57% yield).

$^1$H NMR (250 MHz, DMSO-$d_6$) δ: 1.74 (2H, quintet, J=6.52 Hz, $CH_2$), 3.25–3.44 (2H, m, $CH_2$), 3.50 (2H, broad t, J=5.80 Hz, $CH_2$), 4.53 (1H, broad s, OH), 7.76–8.00 (2H, m, Ar), 8.04–8.36 (4H, m, Ar), 8.56 (1H, d, J=1.55 Hz, Ar), 8.89 (1H, t, J=5.42 Hz, NH). $^{13}$C NMR (250 MHz, DMSO-$d_6$) δ: 32.32, 36.96, 58.68, 125.50, 126.83, 126.85, 127.05, 132.79, 133.04, 133.08, 134.45, 134.66, 139.49, 164.62, 182.11.

Example 4

Preparation of N-(3-cyanoethoxy(diisopropylamino)phosphinoxy)propyl)-2-anthraquinonecarboxamide (3)

N-(3-Hydroxypropyl)-2-anthraquinonecarboxamide (2) (1.00 g, 3.23 mmol) was suspended in anhydrous $CH_2Cl_2$ (30 ml) under $N_2$. N,N-diisopropylethylamine (1.24 ml, 7.12 mmol) was added with stirring followed by dropwise addition of 2-cyanoethyl N,N-diisopropylphosphoramidochloridite (0.72 ml, 3.23 mmol). The resulting slightly turbid reaction mixture was stirred at room temperature for 25 min. The mixture was filtrated and diluted with ethyl acetate (100 ml) containing triethylamine (10 ml) and washed with saturated aqueous $NaHCO_3$ (2×20 ml). The organic solution was dried ($Na_2SO_4$) and evaporated under reduced pressure. The residue was dissolved in a minimum amount of $CH_2Cl_2$ and added dropwise to vigorously stirred ice cooled light petroleum ether (200 ml). The precipitated yellow powder was collected by filtration and dried overnight under high vacuum affording 3 (1.26 g, 77% yield). This compound could be stored under $N_2$ at −20° C. for several months without significant decomposition: $^1$H NMR (250 MHz, CDCl$_3$) δ: 1.17 (d, J=6.86 Hz, $CH_3$), 1.87–2.15 (m, $CH_2$), 2.70 (t, J=5.72 Hz, $CH_2$), 3.41–4.04 (m, $CH_2$, CH), 7.17 (broad t, J=5.49 Hz, NH), 7.76–7.87 (m, Ar), 8.24–8.41 (m, Ar), 8.59 (d, J=1.65 Hz, Ar). $^{13}$C NMR (250 MHz, CDCl$_3$) δ: 20.43, 20.54, 24.58, 24.69, 30.22, 30.33, 38.53, 43.03, 43.23, 58.19, 58.51, 62.45, 62.74, 117.90, 125.04, 127.39, 127.83, 133.15, 133.42, 134.39, 135.04, 139.80, 165.57, 182.50. $^{31}$P NMR (CDCl$_3$) δ: 148.49.

Example 5

Preparation of 2-[2-cyanoethoxy(diisopropylamino)phosphinoxymethyl]anthraquinone (5)

To a stirred suspension of 2-(hydroxymethyl) anthraquinone (Fluka, 1.00 g, 4.20 mmol) in anhydrous $CH_2Cl_2$ (42 ml) under $N_2$, was added 2-cyanoethyl N,N,N',N'-tetraisopropylphosphorodiamidite (1.33 ml, 4.20 mmol) followed by dropwise addition of tetrazole (8.86 ml of a 0.45 M sol. in $CH_3CN$). The reaction mixture was stirred at room temperature for 90 min. and the resultant salts were filtrated off. The filtrate was diluted with $CH_2Cl_2$ (50 ml) and washed with saturated aqueous $NaHCO_3$ (2×20 ml) and brine (20 ml). The organic solution was dried ($Na_2SO_4$) and evaporated under reduced pressure. The remaining yellow solid material was coevaporated with anhydrous $CH_3CN$ and dried over night under high vacuum yielding 5 as bright yellow solid (1.84 g, 100% yield).

$^1$H NMR (400 MHz, CDCl$_3$) δ: 1.23 (d, J=6.96 Hz, $CH_3$), 2.69 (t, J=6.41 Hz, $CH_2$), 3.65–3.75 (m, CH), 3.84–3.97 (m, $CH_2$), 4.82–4.95 (m, $CH_2$), 7.77–7.82 (m, Ar), 8.27–8.32 (m, Ar). $^{13}$C NMR (400 MHz, CDCl$_3$) δ: 20.29, 20.35, 24.50, 24.57, 43.13, 43.26, 58.32, 58.51, 64.48, 64.66, 117.40, 125.03, 127.04, 127.10, 127.41, 132.01, 132.21, 132.48, 133.37, 133.39, 133.89, 133.96, 134.07, 145.95, 146.03, 182.68, 182.89. $^{31}$P NMR (CDCl$_3$) δ: 149.76.

Example 6

Preparation of 5'-end Anthraquinone-ONs

Initially, an unmodified ODN sequence was synthesised on a DNA-synthesizer (Pharmacia Gene Assembler Special®) using standard phosphoramidites coupling conditions according to the protocol (0.2 □mol or 1.3 □mol scale) and standard 2'-deoxynucleoside CPG or polystyrene solid supports. While still on the synthesizer, the 5'-OH termini of the ODN sequence was coupled with the phosphoramidite reagent (3) or (5) using a 0.1 M solution and a 5 min. coupling time. The coupling efficiency was estimated to be >98% as attempted coupling of another thymidine nucleoside (T) residue to a test sequence 5'-anthraquinone-T-3' failed completely (no 4,4'-dimethoxytrityl-release was monitored).

After completion of the synthesis, the desired anthraquinone-ODN was cleaved from the solid support and the nucleobase protection groups were removed by incubation with 32% $NH_4OH$ at 55–60° C. for 10–15 hours. The crude antraquinone-ODN-conjugate was purified by reversed-phase HPLC (C-18, 100 Å, 15 m, 300×3.9 mm ID) in a gradient from 100% 0.05M triethylammonium acetate (pH 7.4) to 100% $H_2O$(50%)/$CH_3CN$(50%), v/v.

TABLE 1

Examples of synthesized antraquinone-ODN conjugates:

| | |
|---|---|
| 1 | 5'-AQCONH($CH_2$)$_3$-aacagctatgaccatg-3' |
| 2 | 5'-AQCONH($CH_2$)$_3$-HEG-aacagctatgaccatg-3' |
| 3 | 5'-AQCONH($CH_2$)$_3$-(HEG)$_2$-aacagctatgaccatg-3' |
| 4 | 5'-AQCONH($CH_2$)$_3$-gtaaaacgacggccagt-3' |
| 5 | 5'-AQCONH($CH_2$)$_3$-HEG-gtaaaacgacggccagt-3' |
| 6 | 5'-AQCONH($CH_2$)$_3$-(HEG)$_2$-gtaaaacgacggccagt-3' |
| 7 | 5'-AQCONH($CH_2$)$_3$-HEG-attaatgctatgcagaaaatctta g-3' |
| 8 | 5'-AQCONH($CH_2$)$_3$-"15-mer non-binding DNA sequence"-GACCGTGTg-3' |
| 9 | 5'-AQCONH($CH_2$)$_3$-"15-mer non-binding DNA sequence"-GACTGTGTg-3' |
| 10 | 5'-AQCH$_2$-($CH_2$)$_3$-gtaaaacgacggccagt-3' |
| 11 | 5'-AQCH$_2$-($CH_2$)$_3$-aacagctatgaccatg-3' |

AQCONH = anthraquinone-2-carboxamide.
HEG = hexaethyloxyglycol.
ON-sequence: lowercase = normal 2'-eoxynudeoside monomers; uppercase = modified nucleosides (Locked Nudeic Acids) LNA ™.

Example 7

Photoimmobilised Anthraquinone-ODN Conjugates Efficiently and Specifically Hybridises with Complementary ODNs in Microtiter Plates Anthraquinone-ODN conjugates 1–6 (Table 1) and unmodified controls ODN-A (5'-aacagctatgaccatg-3') and ODN-B (5'-gtaaaacgacggccagt-3') were synthesised as described. All of the ODNs were diluted in 0.2 M LiCl to a final concentration of 0.1 µM and 100 µL per well were dispensed into a microtiter-plate (MTP, Nunc, Polysorp). The ODN solutions were irradiated for 15 minutes under soft UV light. After irradiation the MTP was washed four times with 300 µL demineralised water. 100 µL per well of 0.004 µM complimentary biotinylated oligomers either 5'-biotin-catggtcatagctgtt-3' (biotin-comp. ODN-A) or 5'-biotin-actggccgtcgttttac-3' (biotin-comp ODN-B) were hybridised to the immobilised oligomers in 2×SSCT (30 mM citrate, 0.3 M NaCl, pH 7.0, 0.1% (v/v) Tween 20) at room temperature for two hours. After washing three times with 300 µL 1×SSCT (15 mM citrate, 0.15 M NaCl, pH 7.0, 0.1% (v/v) Tween 20) and one time phosphate buffered saline (PBST, 0.15 M Na$^+$, pH 7.2, 0.05% (v/v) Tween 20) 100 µL per well 1 µg/mL horse radish peroxidase conjugated streptavidin (Pierce) was added to the MTP. The MTP was incubated for 30 minutes at room temperature and washed three times with 300 µL PBST.

Wells were assayed for peroxidase activity by adding 100 µL of substrate solution (0.1 mL citrate-phosphate buffer pH 5.0, 0.66 mg/mL ortho-pheylenediamine dihydrochloride, 0.012% (v/v) $H_2O_2$) the reaction was stopped after 30 minutes by adding 100 µL 0.5 M $H_2SO_4$ and the absorbance at 492 nm was read in a microtiter-plate reader.

Figure 1:
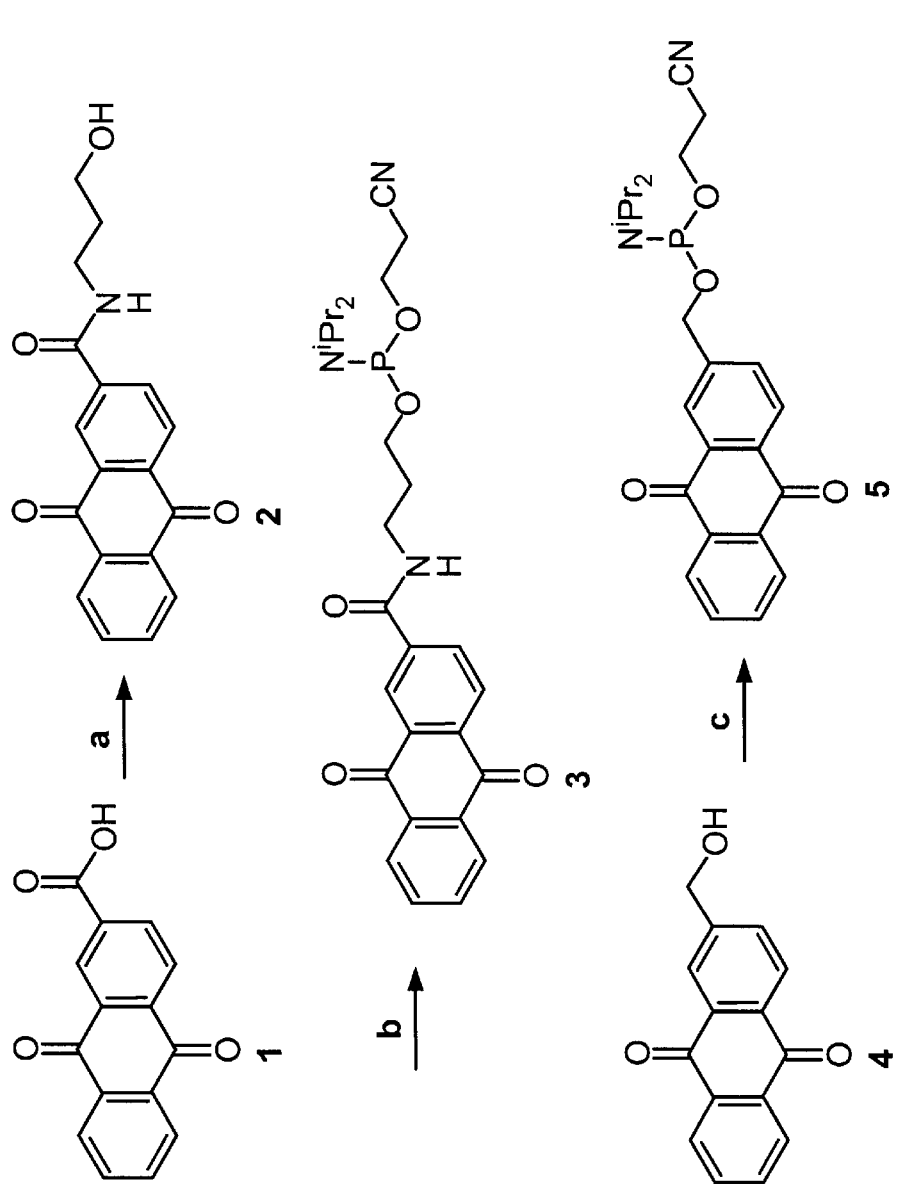
FIG. 1 illustrates the synthesis of anthraquinone phosphoramidites 3 and 5.
Figure 2:
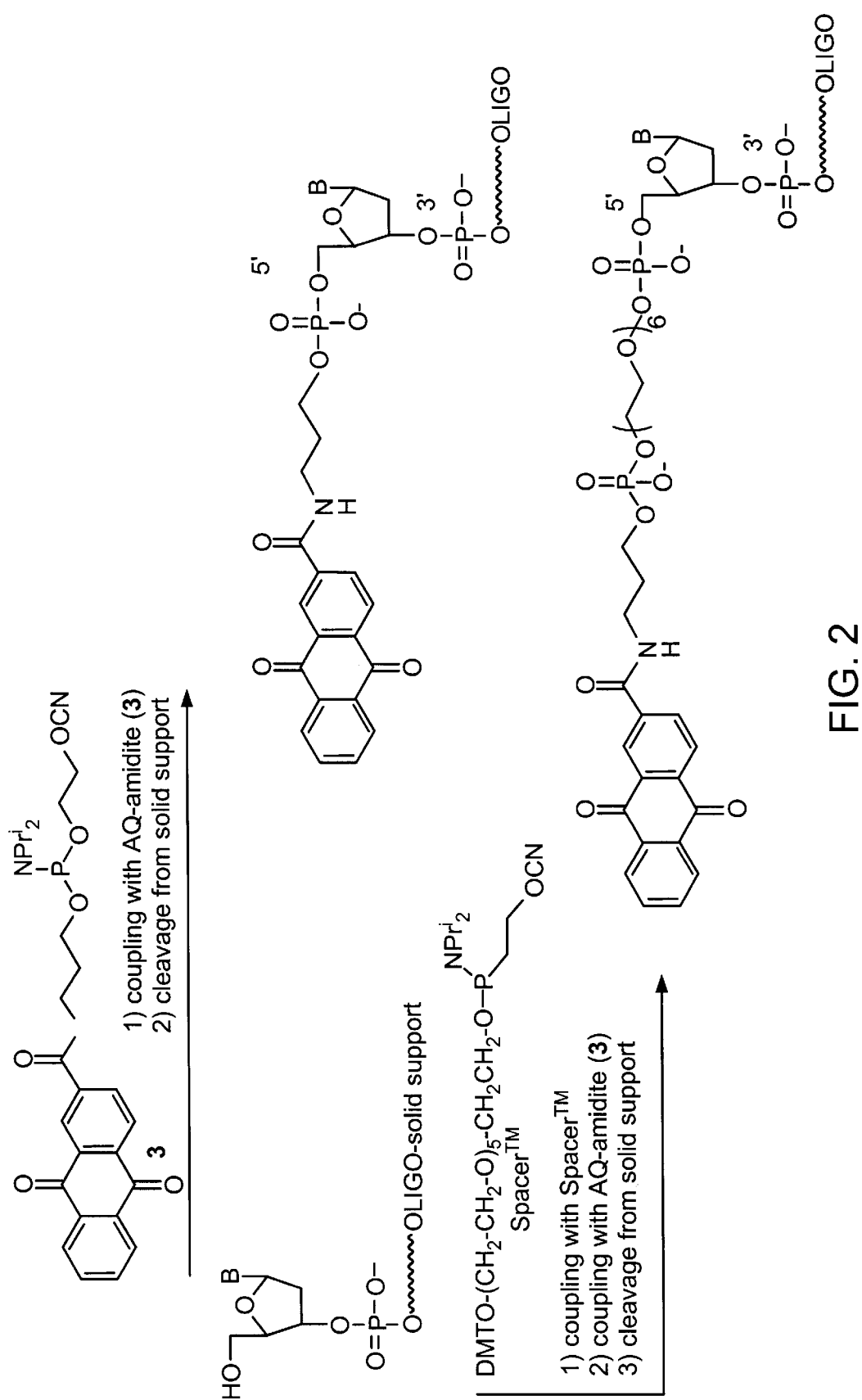
FIG. 2 illustrates the synthesis of two general types of anthraquinone oligonucleotide synthesised.
Figure 3:
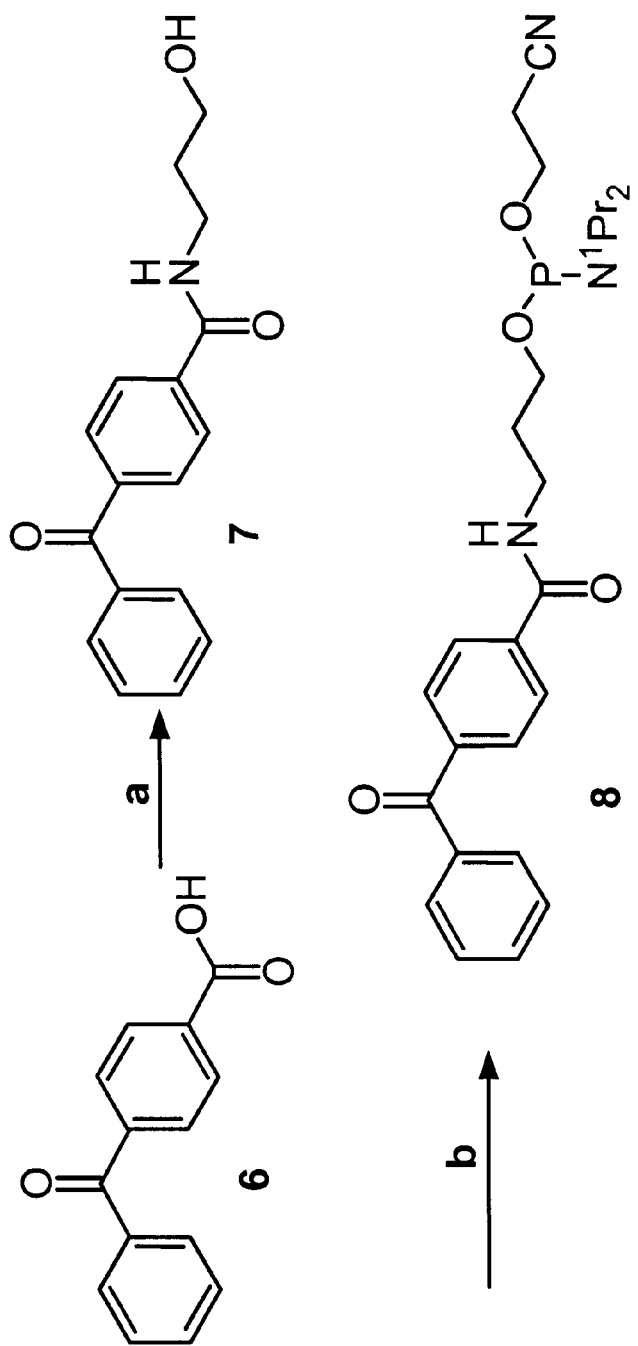
FIG. 3 illustrates the synthesis of a benzophenone-phosphoramidite reagent. Its application for the preparation of benzophenone-oligonucleotide conjugates was analogous to that outlined in FIG. 2 for anthraquinone oligonucleotide conjugates.
Figure 4:
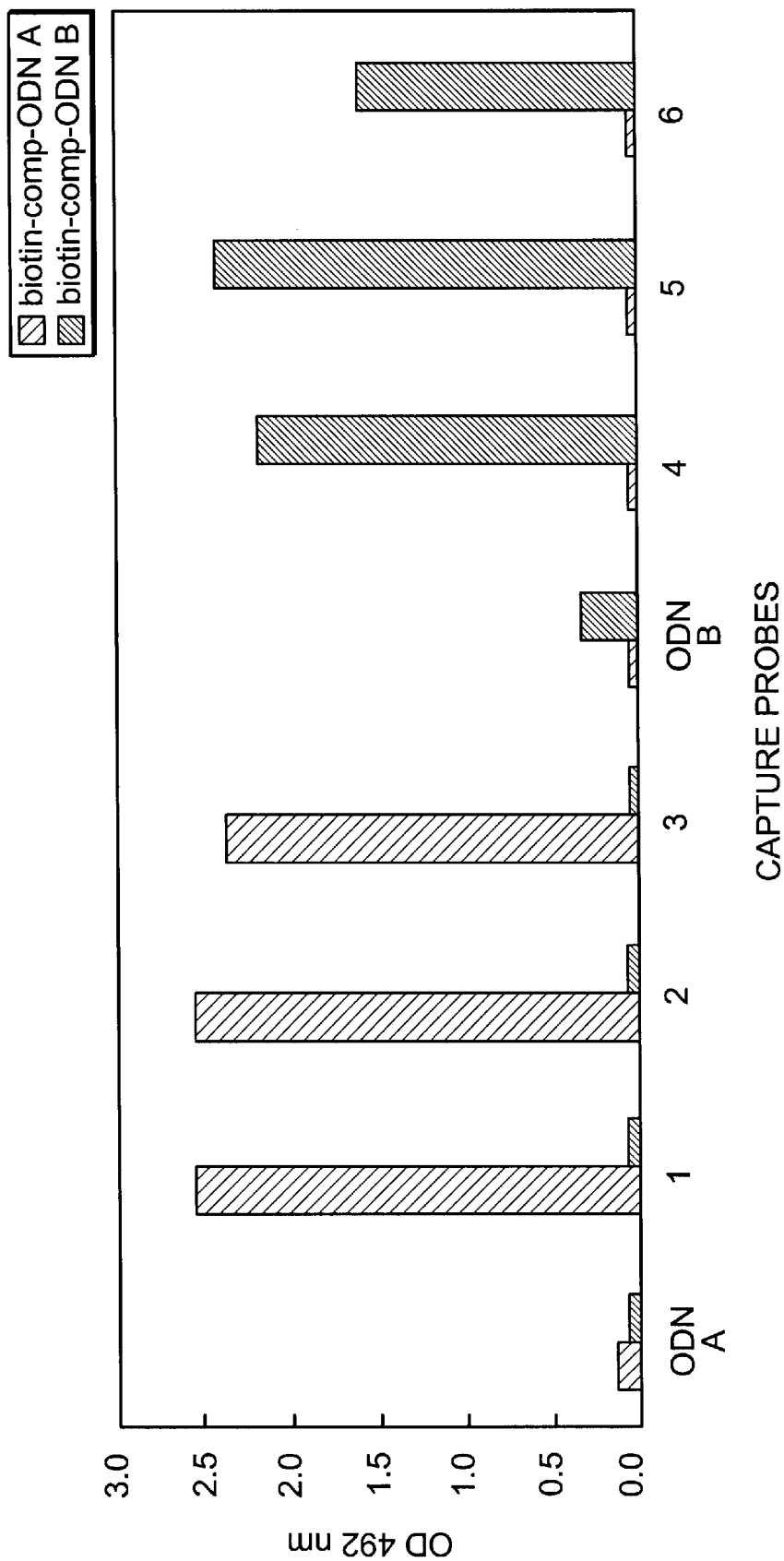
FIG. 4 illustrates that the anthraquinone-ODN conjugates 1–6 (Table 1) capture their specific complimentary biotinylated oligomers very efficiently and significantly better than the corresponding unmodified control-ODN capture probes A and B. No signal is observed when the capture probes are incubated with the unrelated complimentary biotinylated ODNs.

As shown in FIG. 4, the anthraquinone-ODN conjugates 1–6 (Table 1) capture theirs specific complimentary biotinylated oligomers very efficiently and significantly better than the corresponding unmodified control-ODN capture probes A and B. No signal is observed when the capture probes are incubated with the unrelated complimentary biotinylated ODNs.

Example 8

Detection of a Single Nucleotide Polymorphism (SNP) with an Array of Anthraquinone-ON Conjugates Four solutions of Araylt™ Spotting Solution (Telechem, Lot. 99301) were prepared. Solution 1 (positive control): 7 µM ON7 (Table 1), solution 2 (negative control): Pure spotting solution (Neg), solution 3 (wildtype catching probe): 7 µM ON8 (Table 1) and solution 4 (mutant catching probe): 7 µM ON9 (Table 1).

A Cartesian Tech PixSys 3500 spotting robot was programmed to array the 4 different solutions from a microtitre plate onto silanised slides (Manufacturer, Lot.No.). The spots were positioned 1 mm apart in a 4 by 4 array at 30 nL each, 4 replica of each solution according to the following template:

| | | | |
|---|---|---|---|
| Neg | ON8 | ON8 | ON7 |
| ON9 | ON7 | Neg | ON9 |
| ON9 | Neg | ON7 | ON8 |
| ON7 | ON8 | ON9 | Neg |

Subsequent to spotting the spots were allowed to dry for 10 min. at room temperature and then irradiated with UV light for 30 min in a ULS-20-2 illuminator using both upper and lower light and a glass plate holder. Finally the slides were washed in 3×10 min. with Milli-Q water (Ca. 100 mL pr. 25 slides).

In a hybridisation assay, six spotted slides were incubated with different combinations of sample, reporter system and positive controls as described below. Two synthetic 50-mer ODN's, one displaying the mutant-(MT) and one displaying the wildtype (WT) nucleotide sequence of the gene containing the SNP in question, were used as samples. To detect if any sample 50-mer had hybridised to the immobilised catching probes, a 25-mer ODN detection probe complementary to a sequence common to both mutant and wildtype 50-mers, and marked with a biotin in the 5'-end, was used (5'-Biotin-ttggaagtgccctgcagctt-3', ODN-Bio). The presence of biotin was detected by incubation with Cy5-labeled streptavidin (SA/Cy5). As positive control was used a ODN complementary to ON7 and marked with a Cy5 fluorophore in the 5'-end (Pos-Cy5: 3'-ctaagatfttctgcatagcattaat-Cy5-5').

The slides were incubated with 20 μL of hybridisation mix under a cover slide at 37° C. for 30 min. The following six different hybridisation mixtures were used (all in 2×SSC):

| | |
|---|---|
| 1. "Homozygote" wildtype sample @ 0.1 μM: | 3.6 μL WT 50-mer (Stock: 2.8 μM)<br>47.2 μL ODN-Bio (Stock: 1.06 μM)<br>1.0 μL Pos-Cy5 (Stock: 1.0 μM)<br>40 μL 5 × SSC, 0.1% SDS (2 × SSC final)<br>8.2 μL Milli-Q water. |
| 2. "Homozygote" mutant sample @ 0.1 μM: | 7.1 pL MT 50-mer (Stock: 1.4 μM)<br>47.2 μL ODN-Bio (Stock: 1.06 μM)<br>1.0 μL Pos-Cy5 (Stock: 1.0 μM)<br>40 μL 5 × SSC, 0.1% SDS (2 × SSC final)<br>4.7 μL Milli-Q water. |
| 3. "Heterozygote" sample @ 0.1 μM: | 3.6 μL WT 50-mer (Stock: 2.8 μM)<br>7.1 μL MT 50-mer (Stock: 1.4 μM)<br>47.2 μL ODN-Bio (Stock: 1.06 μM)<br>1.0 μL Pos-Cy5 (Stock: 1.0 μM)<br>40 μL 5 × SSC, 0.1% SDS (2 × SSC final)<br>1.1 μL Milli-Q water. |
| 4. "Heterozygote" sample @ 0.1 μM, ÷ Pos-Cy5: | 3.6 μL WT 50-mer (Stock: 2.8 μM)<br>7.1 μL MT 50-mer (Stock: 1.4 μM)<br>47.2 μL ODN-Bio (Stock: 1.06 μM)<br>40 μL 5 × SSC, 0.1% SDS (2 × SSC final)<br>2.1 μL Milli-Q water. |
| 5. Positive control only @ 0.01 μM: | 1.0 μL Pos-Cy5 (Stock: 1.0 μM)<br>40 μL 5 × SSC, 0.1% SDS (2 × SSC final)<br>59 μL Milli-Q water. |
| 6. Detection oligo only @ 0.5 μM: | 47.2 μL ODN-Bio (Stock: 1.06 μM)<br>40 μL 5 × SSC, 0.1% SDS (2 × SSC final)<br>12.8 μL Milli-Q water. |

Following hybridisation, the slides were washed 3×5 min with 1×SSC/0.1% SDS (Ca. 50 mL pr. 6 slides) at room temperature, and hybridised with 20 μL SA/Cy5 (2.5 μg/mL in 2×SSC) under a cover slide at room temperature for 30 min. Finally the slides were washed 3×5 min in 1×SSC/0.1% SDS (ca. 50 mL pr. 6 slides), air dried and read in a confocal laser scanner (FIG. 5A). The tiff-image from the laser scanner was analysed using a dedicated image analysis software and the resulting bar-diagram is viewed in FIG. 5B. It clearly demonstrates that the AQ oligos can be used for efficient production of high quality oligonucleotide arrays.

Example 9

Preparation of N-(3-hydroxypropyl)-2-benzophenonecarboxamide (7)

To a solution of 4-benzoylbenzoic acid (Fluka, >98%, 5.0 g, 22.1 mmol) in HPLC grade DMF (70 ml), was added BOP (10.26 g, 23.20 mmol) and triethylamine (5.88 ml, 42.19 mmol) and the resulting mixture was stirred at room temperature for 10 min. 3-Amino-1-propanol (1.78 ml, 23.27 mmol) was added and the reaction mixture was stirred overnight at room temperature. The dark yellow solution was poured into water (400 ml) and the product was extracted with ethyl acetate (3×250 ml). The combined organic layers were washed with brine (100 ml), dried ($Na_2SO_4$) and evaporated under reduced pressure. The residual yellow syrup, which solidified on standing, was recrystallised from ethyl acetate and hexane yielding compound 7 as an off-white solid material (2.38 g, 38% yield). $^1$H NMR (400 MHz, $CDCl_3$) δ: 1.83 (2H, quintet, J=5.86 Hz, $CH_2$), 3.65 (2H, "q", J=5.85 Hz, $CH_2$), 3.76 (2H, t, J=5.68 Hz, $CH_2$), 7.46–7.89 (9H, m, Ar). $^{13}$C NMR (400 MHz, $CDCl_3$) δ: 31.60, 37.66, 60.14, 126.81, 128.30, 129.88, 132.79, 136.75, 137.41, 139.86, 167.29, 195.93.

Preparation of N-(3-(2-cyanoethoxy (diisopropylamino)phosphinoxy)propyl)-2-benzophenonecarboxamide (8)

Alcohol 7 (500 mg, 1.76 mmol) was dissolved in dry $CH_2Cl_2$ (15 ml) under $N_2$. 2-Cyanoethyl N,N,N,'N'-teraisopropylphosphorodiamidite (0.56 ml, 1.76 mmol) and tetrazole (3.80 ml of a 0.45 M sol. in $CH_3CN$, 1.71 mmol) was added and the reaction mixture was stirred at room temperature for 120 min. The formed solid material (tetrazolium salts) was removed by filtration and washed with $CH_2Cl_2$ (20 ml). The combined clear fiftrates were washed with saturated aqueous $NaHCO_3$ (2×30 ml), dried ($Na_2SO_4$) and evaporated under reduced pressure. The crude product was dried under high vacuum affording the phosphoramidite 8 as a pale yellow oil (812 mg, 95% yield), which was used without further purification. $^{31}$P NMR ($CDCl_3$) δ: 148.45.

Attempted precipitation of phosphoramidite 8 (obtained by phosphitylation of 7 with 2-cyanoethyl N,N-phosphoramidochloridite in the presence of N,N-diisopropylethylamine) from $CH_2Cl_2$ or toluene in hexane was not possible, indicating that this material is an oil by nature. However the phosphoramidite 8 can be stored at −20° C. under $N_2$ for several weeks and possibly months without decomposition.

Example 10

Preparation of 5'-end Benzophenone(BP)-oligodeoxynucleotide(ODN) Conjugates

The following two BP-ODN conjugates were synthesized on an EXPEDITE™ 8909 DNA-synthesizer:
1) 5'-BP-CONH($CH_2$)$_3$-HEG-gtaaaacgacggccagt-3'
2) 5'-BP-CONH($CH_2$)$_3$-HEG-aacagctatgaccatg-3'

Standard phosphoramidite coupling conditions according to the protocol of the synthesizer (0.2 μmol scale) and standard 2'-deoxynucleoside CPG solid supports were used to prepare the above oligonucleotide sequences. While still on the synthesizer the 5'-OH termini of the ODNs were coupled with the benzophenone phosphoramidite reagent 8, using a 0.1 M sol. in $CH_3CN$ and standard coupling time (100 sec.). The coupling efficiency of 8 was estimated to be >98% as attempted coupling of another thymidine nucleoside residue to a test sequence: 5'-BP-t-3' failed (with capping disconnected, no 4,4'-dimethoxytrityl-release was observed).

The above BP-ODNs were cleaved from the solid support, deblocked and purified as described previously (Example 6).

The composition of the benzophenone containing oligodeoxynucleotides was verified by MALDI-TOF.

DNA oligomers carrying a 5'anthraquinone or a 5'benzophenone can be covalently immobilized on a solid support by irradiation and the immobilized oligomers are efficient in the capture of a complentary DNA oligomer.

Anthraquinone (AQ) and benzoephenone (BP) oligonucleotides were diluted in water and the concentration was determined at 260 nm (Type A oligomers: AQ1-C3-seq (Table 1, entry 4), AQ1-C3-HEG-seq (Table 1, entry 5), AQ-1-C3-HEG2-seq (Table 1, entry 6), AQ2-C3-seq (Table 1, entry 10) and BP-C3-seq (Example 10, oligo 1). Type B oligomers: AQ1-C3seq (Table 1, entry 1), AQ1-C3HEG-seq (Table 1, entry 2), AQ1-C3-HEG2-seq (Table 1, entry 3), AQ2-C3-seq (Table 1, entry 11) and BP-C3-seq (Example 10, oligo 2). Desired oligo concentrations were diluted in 0.2 M NaCl (12.5 μM) and further 5 fold dilutions were made (2.5, 0.5, 0.1, 0.02, 0.004, 0.0008 μM) in 0.2 M NaCl. For each oligomer 100 μL of each concentration was dispensed per microtiter well. The immobilisation procedure was performed by irradiation with soft UV-light for 15 minutes 10 cm above the microtiter plate (MTP). The MTP was then washed with with 3×300 μL/well demineralised water.

2 μM complementary biotinylated oligonucleotides (complementary to type A oligomers: 5'-biotin-CATGGTCATAGCTGTT-3' and complementary to type B oligmers: 5'-biotin-ACTGGCCGTCGTTTAC-3') were hybridised to the immobilised oligonucleotides in 100 μL/well 2×SSCT (30 mM citrate, 0.3 M NaCl, pH 7.0, 0.05% C(Vv) Tween 20) for 60 minutes at 37° C. The MTP was washed with 3×300 μL/well phosphate buffered saline (1×PBST, 0.15+, pH 7.2, 0.05% (v/v) Tween 20) and incubated with 100 μL/well 1 μg/mL streptavidin conjugated with horse radish peroxidase diluted in 1×PBST at 37° C. for 15 minutes. After washing with 3×300 μL/well 1×PBST a simple calorimetric endpoint measurement was obtained after addition of 0.66 mg ortho-phenylenediamine, 0.1 M citrate-phosphate buffer, pH 5.0, 0.012% $H_2O_2$ (100 μL/well). The reaction was stopped 90 sec. after adding 100 μL/well 0.5M $H_2SO_4$ and the absorbency was measured in a microtiter plate reader at 492 nm.

As shown in FIGS. 6 and 7 both the AQ oligomers and the BP oligomers yield a clearly concentration dependent signal. When using a non-complementary sequence no signal could be detected. We conclude that both AQ and BP oligomers can be covalently attached to a solid surface by irradiation with similar efficiencies and that oligomers attached in this way are able to hybridise to their complementary target DNA oligomers.

What is claimed is:

1. A phosphoramidite reagent of the formula I

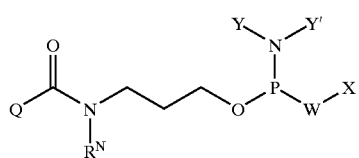

(I)

wherein Y and Y' each independently are selected from optionally substituted $C_{1-6}$-alkyl or Y and Y' together with the nitrogen to which they are bonded form a non-aromatic N-heterocyclic ring; W is selected from O and S; X is selected from optionally substituted $C_{1-8}$-alkyl and optionally substituted benzyl; $R^N$ is selected from hydrogen $C_{1-4}$alkyl, optionally substituted benzyl, optionally substituted quinones, and nucleosides; and Q is selected from optionally substituted quinones and optionally substituted photoreactive ketones.

2. A reagent according to claim 1, wherein $R^N$ is hydrogen.

3. A reagent according to any of the preceding claims, wherein Q is a quinone or an optionally substituted benzophenone.

4. A reagent according to claim 3, wherein the quinone is anthraquinone.

5. A reagent according to claim 3, wherein the quinone is phenanthrenequinone.

6. A reagent according to claim 3, wherein Q is benzophenone.

7. A reagent according to any of the preceding claims, wherein Y and Y' are selected from ethyl and isopropyl, in particular isopropyl.

8. A reagent according to claim 7, wherein Y and Y' both are isopropyl.

9. A reagent according to any of claims 1–6, wherein Y and Y' together with the nitrogen to which they are bonded form a morpholino ring.

10. A reagent according to any of the preceding claims, wherein X designates 2-cyanoethyl and W designates O.

11. A reagent according to claim 1, which is

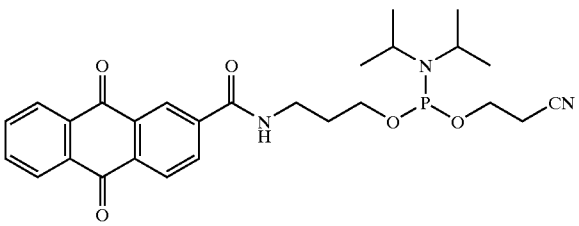

12. A reagent according to claim 1, which is

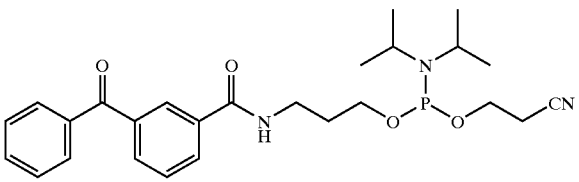

13. An oligomer comprising the following fragment:

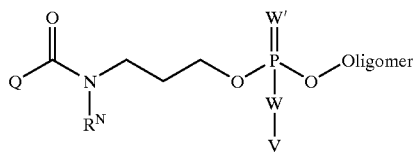

wherein $R^N$ is selected from hydrogen, $C_{1-4}$-alkyl, optionally substituted benzyl, optionally substituted quinones, and nucleosides; Q is selected from optionally substituted quinones and optionally substituted photoreactive ketones; W and W' are independently selected from O and S; and V is selected from optionally substituted $C_{1-6}$-alkyl, optionally substituted benzyl, hydrogen, Li+, K+, Na+, and $NH_4^+$.

14. An oligomer according to claim 13, wherein $R^N$ is hydrogen and Q is selected from anthraquinone and optionally substituted benzophenone.

15. An oligomer according to claim 13, wherein $R^N$ is hydrogen and Q is phenanthrenequinone.

16. An oligomer according to claim 13, wherein $R^N$ is hydrogen and Q is benzophenone.

17. A phosphoramidite reagent of the formula II

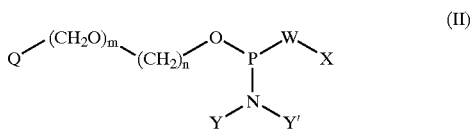

(II)

wherein Y and Y' each independently are selected from optionally substituted $C_{1-6}$-alkyl or Y and Y' together with the nitrogen to which they are bonded form a non-aromatic N-heterocyclic ring; X is selected from optionally substituted $C_{1-6}$-alkyl and optionally substituted benzyl; W is selected from O and S; Q is selected from optionally substituted quinones and optionally substituted photoreactive ketones; n is an integer from 1 to 10; and m is 0 or 1.

18. An oligomer comprising the following fragment:

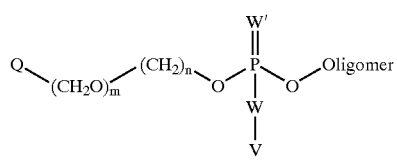

wherein Q, W, W', V, n and m are as defined in claim 16.

19. An oligomer according to claim 18, wherein Q is anthraquinone, m is 0 and n is 1.

20. An oligomer according to claim 18, wherein Q is an optionally substituted benzophenone, m is 0 and n is 1.

21. An oligomer according to claim 18, wherein Q is phenanthrenequinone, m is 0 and n is 1.

22. An oligomer according to claim 18, wherein Q is benzophenone, m is 0 and n is 1.

* * * * *